United States Patent [19]

Meadows et al.

[11] Patent Number: 5,156,616
[45] Date of Patent: Oct. 20, 1992

[54] APPARATUS AND METHOD FOR SUTURE ATTACHMENT

[76] Inventors: Bruce F. Meadows, 6 Monte Sano Ct., Hanahan, S.C. 29406; William S. Ogden, 101 N. Madison, Whiteville, N.C. 28472

[21] Appl. No.: 832,964

[22] Filed: Feb. 10, 1992

[51] Int. Cl.⁵ .............................................. A61B 17/00
[52] U.S. Cl. ...................................... 606/232; 606/73; 411/395
[58] Field of Search .................... 606/72, 73, 86, 232; 411/395

[56] References Cited

U.S. PATENT DOCUMENTS

| | | | |
|---|---|---|---|
| 4,507,817 | 4/1985 | Staffeld | 411/395 |
| 4,537,185 | 8/1985 | Stednitz | 606/73 |
| 4,738,255 | 4/1988 | Gable et al. | 606/86 |
| 4,976,715 | 12/1990 | Bays et al. | 411/395 |
| 5,019,079 | 5/1991 | Ross | 606/72 |
| 5,037,422 | 8/1991 | Hayhurst et al. | 606/72 |
| 5,047,030 | 9/1991 | Draenert | 606/73 |

Primary Examiner—Stephen C. Pellegrino
Assistant Examiner—Gary Jackson
Attorney, Agent, or Firm—Woodard, Emhardt, Naughton Moriarty & McNett

[57] ABSTRACT

A cannulated bone screw is illustrated that retains a knotted suture and which is anchored to bone. The cannulated bone screw comprises a biocompatible body having a proximal end and a distal end, and the body includes exterior screw threads for inserting and retaining the body into the bone. The body is cylindrical and has a passageway that extends axially therethrough. The passageway includes a central portion, a distal portion and a proximal portion. The central portion has a diameter less then the distal portion and is sized to receive a suture thread therethrough. The distal portion is sized to receive a suture thread knot. The suture thread knot received within the distal portion is retained by the central portion, which is sufficiently small to prevent the knot from being drawn therethrough. The proximal portion includes a hexagonal cavity for cooperating with an external drive tool for rotating the body and thereby driving the body into the bone.

11 Claims, 3 Drawing Sheets

APPARATUS AND METHOD FOR SUTURE ATTACHMENT

BACKGROUND OF THE INVENTION

1. Field of the Invention

This invention relates to appliances and methods for use in orthopedic surgical procedures to anchor a suture to a bone. After attachment to the bone, the suture may be used, for example, to attach a ligament to the bone.

2. Description of the Prior Art

Certain orthopedic surgery procedures require that a ligament be reattached to bone. Such ligament reattachment may occur, for example, in knee or elbow procedures. Various types of anchors have been used in the past to anchor the suture to bone. These anchors are generally made of biocompatible stainless steel or similar non-corrosive metal. Suture thread is attached to the anchor and the anchor is inserted into the bone. Prior art anchors generally lack a simple attachment of the suture thread thereto and may require cement for sufficient attachment strength.

When a torn ligament must be reattached to bone, the torn end must be anchored to the bone and placed in close proximity to allow the ligament to grow into the bone mass and reattach itself. Various prior art devices are unsuited for use in areas having spacial constraints. The manipulations required to set the anchor into bone also reflect upon the ability of the anchor to operate in locations having spacial constraints. If a bone anchor is unsuitable for placement in the original location of ligament attachment, a nearby location having suitable space must be utilized. The closer the suture is anchored to the original point of attachment of the ligament, the better for body mechanics. Design limitations of prior art devices have limited the optimal placement of the suture anchor and have lead to less efficient attachment of ligaments.

SUMMARY OF THE INVENTION

Briefly describing one aspect of the present invention, there is provided a cannulated bone screw useful for anchoring a suture thread to bone. The cannulated bone screw is comprised of a biocompatible body having a proximal end and a distal end. The body includes exterior screw threads for inserting and retaining the cannulated bone screw into bone. The body also defines a passageway extending therethrough, which includes a central portion and a distal portion. The central portion is sized to receive a suture thread therethrough and the distal portion is sized to receive a knotted end of the suture thread. The central portion is sized smaller than the distal portion, in such a manner that the central portion is sufficiently large to receive a suture thread therethrough, but sufficiently small to prevent a knot in the suture thread from being drawn therethrough. The body further defines a means for cooperating with an external drive tool for rotating the body and thereby driving the body into the bone.

It is an object of the present invention to provide a simplified attachment of a suture to a bone screw. It is another object of the present invention to provide a cannulated bone screw for anchoring a suture to bone near the prior point of ligament attachment. It is a further object of the present invention to provide a bone screw in which the body is cylindrical and has a central axis in which the passageway extends axially therethrough.

Further objects and advantages of the present invention will be apparent from the description of the preferred embodiment which follows.

DESCRIPTION OF THE PREFERRED EMBODIMENT

For the purposes of promoting an understanding of the principles of the invention, reference will now be made to the preferred embodiment of the present invention and specific language will be used to describe the same. It will nevertheless be understood that no limitation of the scope of the invention is thereby intended, such alterations and further modifications, and such further applications of the principles of the invention therein being contemplated as would normally occur to one skilled in the art to which the invention relates.

The cannulated bone screw of the present invention provides attachment of suture thread in a simpler, more secure manner. The cannulated bone screw may be utilized, for example, to anchor sutures near the original point of attachment of a ligament to bone, and also saves the physician time in his procedures. The suture may be provided pre-knotted and received into the bone screw and mated with the external driver, so that the orthopedic surgeon need merely anchor the screw into the bone and attach the suture to the ligament.

Figure 1:
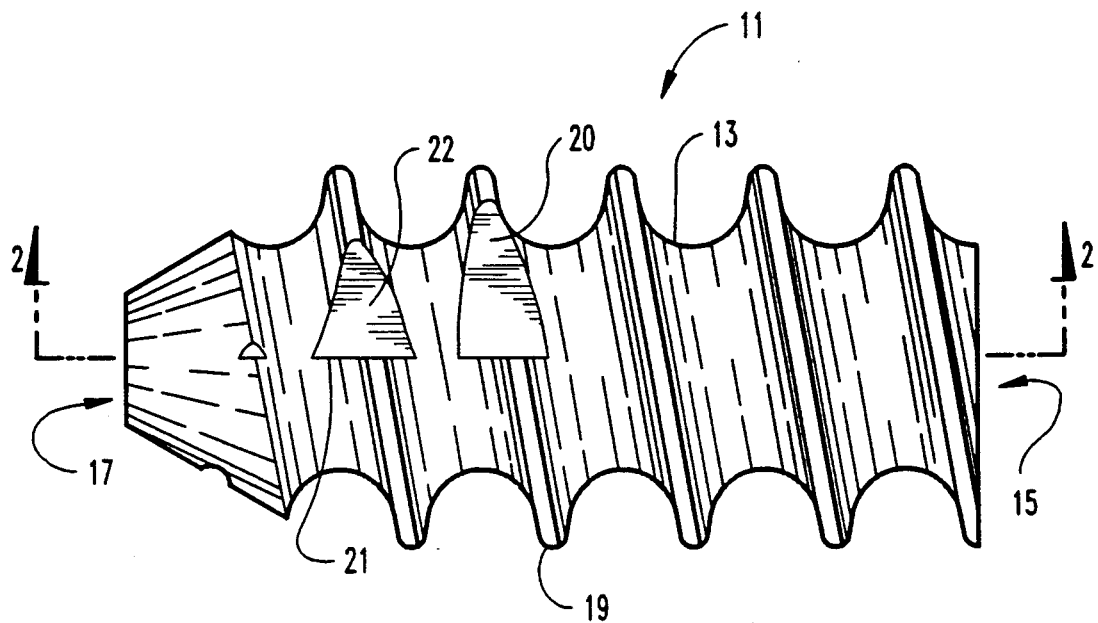
FIG. 1 is a side elevation view of a self-tapping cannulated bone screw constructed in accordance with the present invention.
Figure 2:
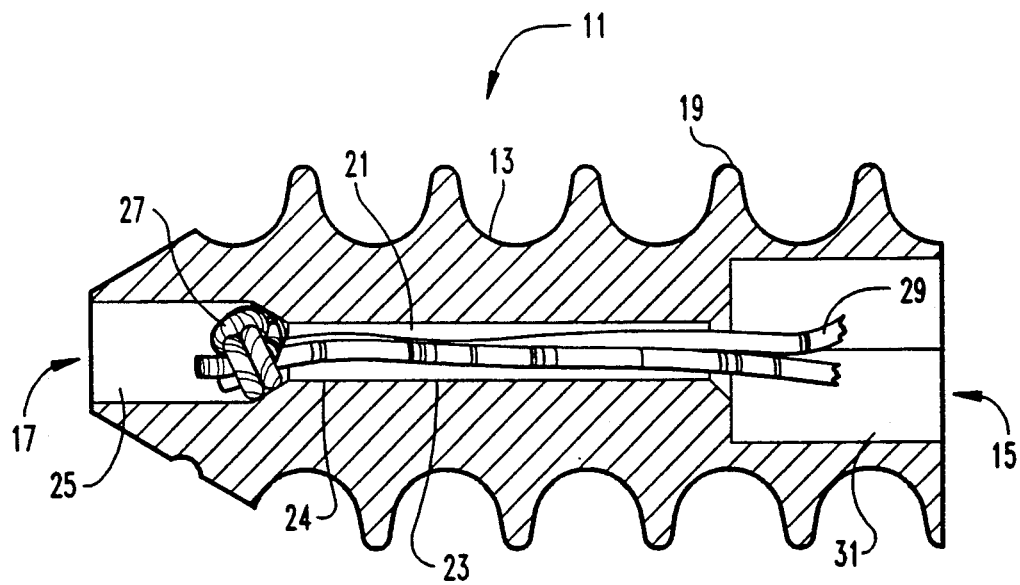
FIG. 2 is a section view of a bone screw of the present invention, taken along the line 2—2 in FIG. 1, and looking in the direction of the arrows.

Referring to FIGS. 1 and 2, a preferred cannulated bone screw 11 is illustrated. The cannulated bone screw is comprised of a biocompatible body 13 having a proximal end 15 and a distal end 17. Exterior screw threads 19 are located on the body and are used for inserting and retaining the body into bone. Three flats 20 are cut longitudinally into the body 13, as seen in FIG. 1. Each of the flats has a radial face 21 and a perpendicular root face 22. The cutting edge is located on the radial face (see FIG. 3).

The body is generally formed from a type of biocompatible material, typically metal. The preferred material is TI-6AL-4V EL1 which meets ASTM F 136 specifications. The surface of the body preferably receives a glass bead blast and is coated with a titanium nickel coating. This material is biocompatible and is suitable for implantation into human bone. Other such biocompatible materials having the required tensile properties and having approval for use in humans are well known in the art, and may similarly be utilized.

A passageway 23 extends through the body 13, and includes a central portion 24 and a distal portion 25. The distal portion is sized to receive a suture thread knot 27. Central portion 24 is sized to receive a suture thread therethrough. However, central portion 24 is sized sufficiently smaller than the distal portion 25 such that the suture thread knot 27 is prevented from being drawn therein.

A simple and effective method is provided for attaching a suture thread to the cannulated bone screw. The suture thread is passed through the passageway 23 of the cannulated bone screw and a knot is tied in the suture thread extending from the distal end of the passageway. The suture thread is then withdrawn from the proximal end while the knot is advanced through the distal section until it abuts the central portion. The central portion has a smaller cross-sectional area than the knot and blocks the passage of the knot thereby anchoring the suture thread.

The body further defines means for cooperating with an external drive tool for rotating the body and thereby driving the body into the bone. In the preferred embodiment, the means for cooperating with the external drive tool is a hexagonally-shaped, proximal cavity 31. A corresponding external hex-driver 51 mates with the hexagonal cross-section 45 (See FIGS. 4 and 5). Various other means for cooperating with an external drive tool may also be provided. For example, grooves could be provided to mate with a flat drive head, a Phillips drive head, or other suitable means for linking a rotating shaft to the cannulated bone screw.

The preferred embodiment of the cannulated bone screw utilizes self-tapping exterior screw threads to simplify the process of anchoring the cannulated bone screw to bone and thereby anchor the suture to bone. The self-tapping screw threads are designed to engage and anchor the cannulated bone screw into a bore prepared by a suitably sized bone drill. Alternative embodiments may utilize a head capable of both boring and tapping into the bone.

Figure 3:
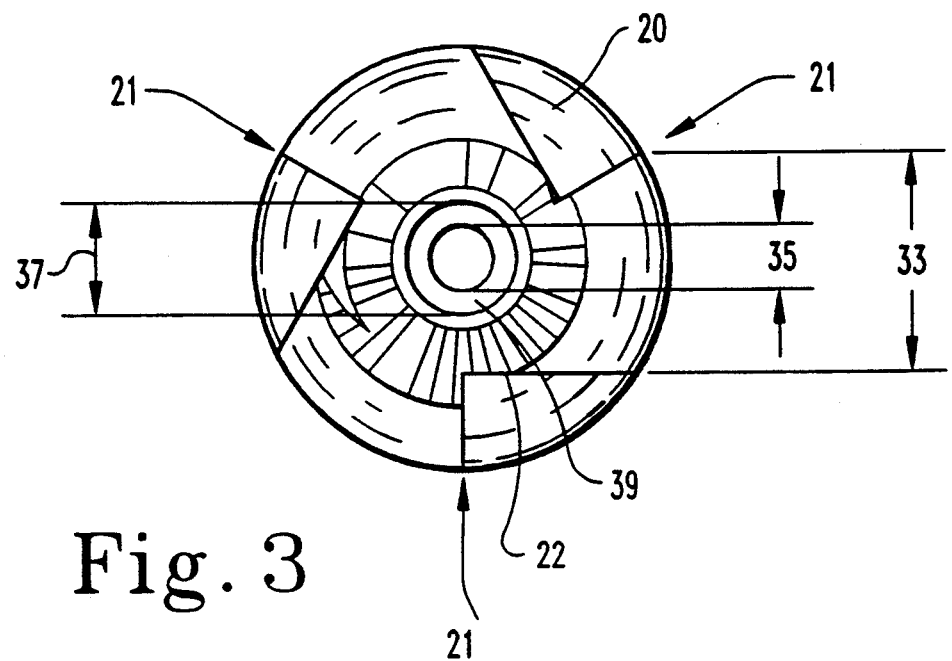
FIG. 3 is a distal end elevational view of the bone screw of FIG. 1.
Figure 4:
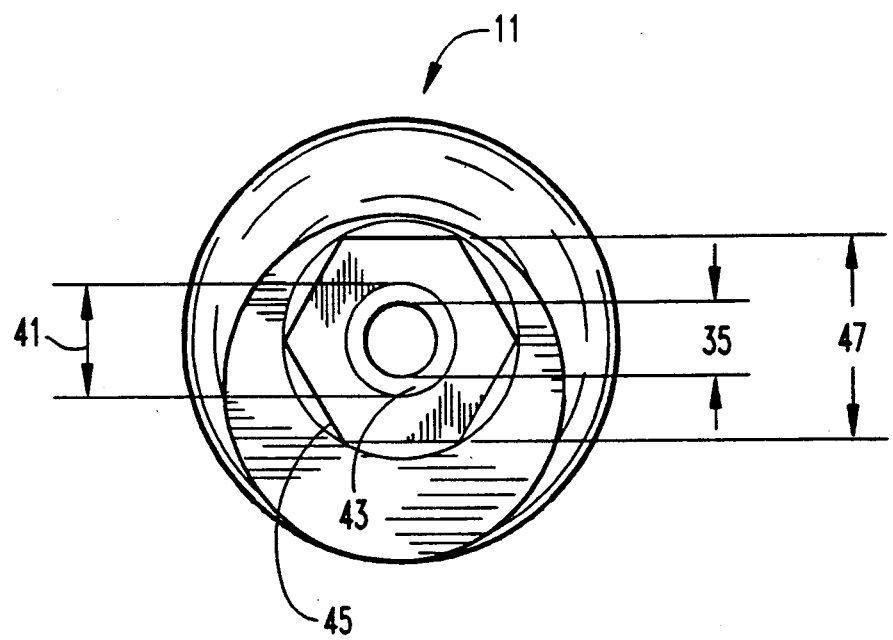
FIG. 4 is a proximal end elevation view of the bone screw of FIG. 1.

Referring to FIGS. 3 and 4, an elevation view of the distal end and proximal end of the cannulated bone screw are shown. Three flats 20 are cut longitudinally into the body 13 and are spaced at approximately 120 degree intervals (See FIG. 1). These flats are cut three threads deep into the distal end of the cannulated bone screw. Each of the flats has a radial face 21 and a perpendicular root face 22 even with the root diameter 33. Each radial face has an edge that serves as a cutting edge.

The distal view illustrates the central portion diameter 35 and the distal portion diameter 37. The central portion diameter 35 is substantially less than the distal portion diameter 37. This difference in diameter allows the knot of a knotted suture thread to pass through the distal end and be retained within the tip of the bone screw as the suture thread is pulled through the passageway. The central portion diameter 35 is sufficiently large as to receive a suture thread therethrough but sufficiently small as to prevent the knot 27 from being drawn therethrough. The free ends of the suture thread (FIG. 6) may be pulled through the proximal end of the passageway until the knot reaches the central portion 35, where it is securely held. A beveled portion 39 is formed between the distal and central portions that allows the knot 27 (FIG. 2) to be compressed as tension is placed on it from the suture thread 29. This compression of the knot dissipates the forces upon it and adds to its resistance to breakage.

FIG. 4 illustrates a front elevational view of the proximal end of the bone screw 11. This view illustrates the central portion diameter 35, the proximal portion diameter 41, and the beveled portion 43 between the central portion and the proximal portion. The means for cooperating with an external drive tool is shown to be preferably hexagonal in cross-section. The hexagonal cross-section 45 has a dimension 47 which corresponds to a hex-driver that mates therewith and is utilized to rotate the cannulated bone screw (FIG. 5).

Figure 5:
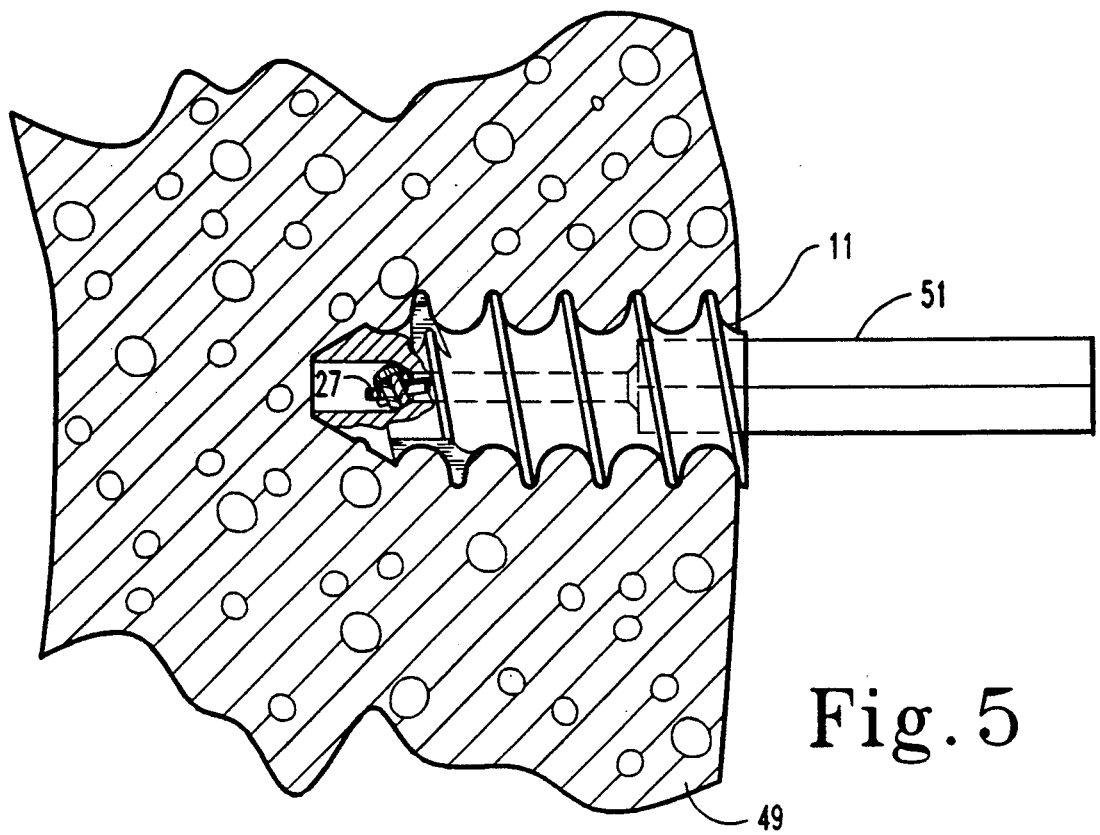
FIG. 5 is a cross-sectional view showing a bone screw of the present invention as inserted by an external driver into a bone mass.
Figure 6:
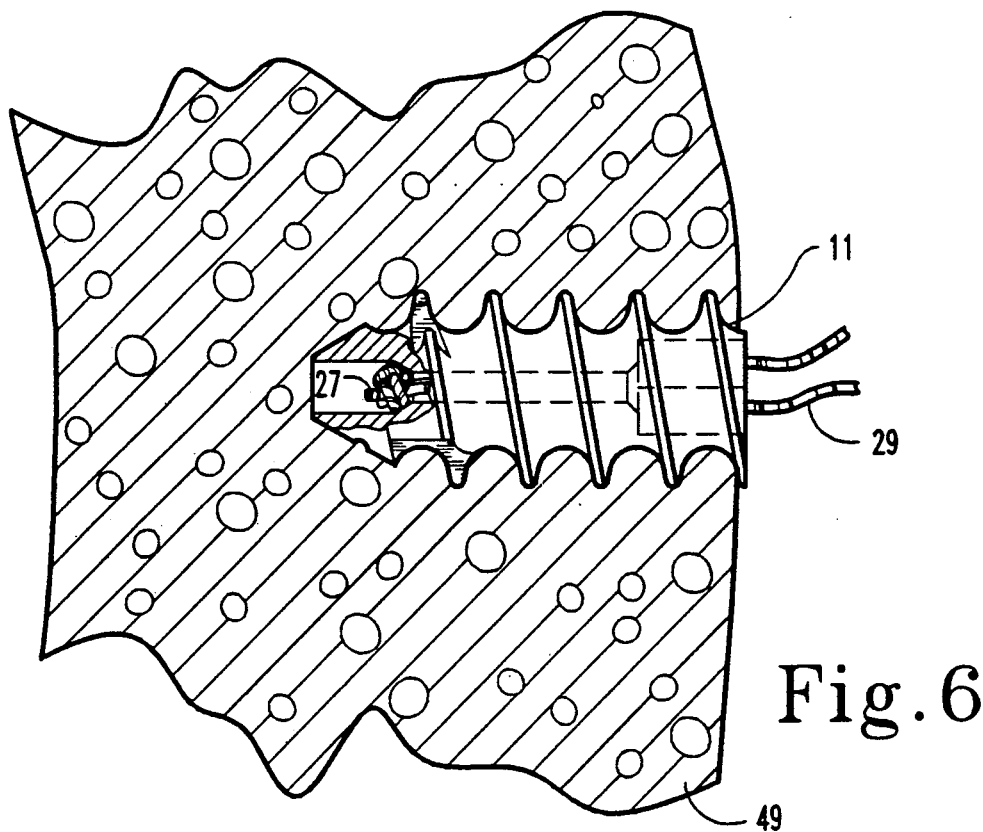
FIG. 6 is a cross-sectional view of the bone screw and bone mass of FIG. 5, and further showing the free ends of the suture threads extending therefrom.

Referring to FIGS. 5 and 6, the cannulated bone screw 11 is shown anchored into bone 49. FIG. 5 illustrates an external hex-drive 51 inserted into the proximal end of cannulated bone screw 11 as it is driven into the bone 49. The knot 27 may also be seen. The external hex-driver 51 may include a groove to allow the suture thread to pass between it and the cannulated bone screw, or it may have a bore or passageway to allow the suture thread to be retained within the driver while the bone screw is being driven into the bone. In alternative embodiments, the proximal cavity may also have a longitudinal groove to allow the suture thread 29 to pass between the groove and the external hex-driver.

FIG. 6 illustrates the cannulated bone screw 11 anchored into bone 49 with the knot 27 retained by the central portion of the passageway and the free ends of the suture thread 29 anatomically positioned to allow connection of ligaments or other suitable structures thereto.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A cannulated bone screw useful for anchoring a suture thread to bone which comprises:
   a biocompatible body having a proximal end and a distal end, said body including exterior screw threads for inserting and retaining said body into the bone,
   said body defining a passageway extending therethrough, the passageway including a central portion and a distal portion, the central portion being sized to receive a suture thread therethrough, the distal portion being sized to receive a suture thread knot, the central portion being sized smaller than the distal portion, the central portion being sufficiently large as to receive a suture thread therethrough but sufficiently small as to prevent a suture thread knot from being drawn therethrough,
   said body further defining means for cooperating with an external drive tool for rotating said body and for thereby driving said body into the bone.

2. The bone screw of claim 1 in which said body defines self-tapping exterior screw threads.

3. The bone screw of claim 1 in which said body is cylindrical and has a central axis, and in which the passageway extends axially therethrough.

4. The bone screw of claim 3 in which said body defines self-tapping exterior screw threads.

5. The bone screw of claim 1 in which said means for cooperating with an external drive tool comprises a proximal cavity configured to receive an external drive tool.

6. The bone screw of claim 5 in which the proximal cavity is sized larger than the central portion of the passageway and has a hexagonal cross-section for cooperation with an external hex driver.

7. The bone screw of claim 5 in which said body defines self-tapping exterior screw threads.

8. The bone screw of claim 5 in which said body is cylindrical and has a central axis, and in which the passageway extends axially therethrough.

9. The bone screw of claim 8 in which said body defines self-tapping exterior screw threads.

10. The bone screw of claim 9 in which the proximal cavity is sized larger than the central portion of the passageway and has a hexagonal cross-section for cooperation with an external hex driver.

11. A method of attaching suture thread to bone which comprises the steps of:
   a. providing a bone screw comprising a biocompatible body having a proximal end and a distal end, said body including exterior screw threads for inserting and retaining said body into the bone, said body defining a passageway extending therethrough, the passageway including a central portion and a distal portion, the central portion being sized to receive a suture thread therethrough, the distal portion being sized to receive a suture thread knot, the central portion being sized smaller than the distal portion, the central portion being sufficiently large as to receive a suture thread therethrough but sufficiently small as to prevent a suture thread knot from being drawn therethrough, said body further defining means for cooperating with an external drive tool for rotating said body and for thereby driving said body into the bone;
   b. passing suture thread through the passageway of the body of said bone screw to extend from the distal end;
   c. tying a knot in the suture thread extending from the distal end of the passageway;
   d. withdrawing the suture thread from the proximal end of said bone screw and thereby drawing the knot into the distal section until it abuts the central portion having a smaller cross-sectional area, thereby blocking the passage of the knot; and
   e. inserting said bone screw into the bone.

* * * * *